United States Patent [19]

Gascoyne et al.

[11] 4,069,345

[45] Jan. 17, 1978

[54] COMPOSITIONS HAVING A PHYSIOLOGICAL COOLING EFFECT

[75] Inventors: John M. Gascoyne, Southall; Roger Hems, Maidenhead; David J. Spring, Datchet, all of England

[73] Assignee: Wilkinson Sword Limited, London, England

[21] Appl. No.: 498,173

[22] Filed: Aug. 16, 1974

[30] Foreign Application Priority Data

Aug. 22, 1973 United Kingdom ............... 39729/73

[51] Int. Cl.² ........................................... A61K 31/045
[52] U.S. Cl. .................................................. 424/343
[58] Field of Search ......................................... 424/343

[56] References Cited

U.S. PATENT DOCUMENTS

| 2,001,046 | 5/1975 | Welch ................................. 424/343 |
| 3,511,914 | 5/1970 | Wolkoff et al. ....................... 424/343 |
| 3,644,653 | 2/1972 | Tcheitcheff ........................... 424/358 |

FOREIGN PATENT DOCUMENTS 1,315,626  5/1973  United Kingdom ................ 424/343

OTHER PUBLICATIONS

Remington's Pharmaceutical Sciences, 13th Edition, (1965), p. 855.
Wilson et al., Textbook of Organic Medicinal and Pharmaceutical Chemistry, Fourth Edition, (1962), pp. 111-112.
Chemical Abstracts, Eighth Collective Index, (1967-1971), vols. 66-75, pp. 18623s-18627s.
Chemical Abstracts, Seventh Collective Index, (1962-1966), vols. 56-65, pp. 13780s-13782s.

*Primary Examiner*—Norman A. Drezin
*Attorney, Agent, or Firm*—Leydig, Voit, Osann, Mayer & Holt, Ltd.

[57] ABSTRACT

Alkyl-substituted methanols are disclosed having the property of stimulating the cold receptors of the nervous system of the human body to produce a cold sensation and are used for this purpose in a variety of edible and topical preparations.

4 Claims, No Drawings

COMPOSITIONS HAVING A PHYSIOLOGICAL COOLING EFFECT

FIELD OF INVENTION

This invention relates to compositions and compounds having a physiological cooling effect on the skin and on the mucous membranes of the body, particularly those of the mouth, nose, throat and gastrointestinal tract.

BACKGROUND OF THE INVENTION AND PRIOR ART

Menthol is well known for its physiological cooling effect on the skin and mucous membranes of the mouth and has been extensively used as a flavouring agent (menthol being a major constituent of oil of peppermint) in foodstuffs, beverages, dentifrices, mouthwashes, etc. and as a component in a wide range of toiletries, liniments and lotions for topical application. Menthol is also a well known tobacco additive for producing a 'cool' sensation in the mouth when smoking.

It is well established that the 'cooling' effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use, in some compositions, is circumscribed by its strong minty odour and its relative volatility.

A few other compounds have been reported in the technical literature as having an odour or flavour similar to menthol and from time to time have been proposed as flavourants or odourants in a variety of topical and ingestible compositions. For example, Japanese Patent Publication No. 39-19627 reports that 3-hydroxymethyl p-menthane (menthyl carbinol) has a flavour closely resembling that of l-menthol and suggests its use as a flavourant in confectionery, chewing gum and tobacco. In Swiss Pat. No. 484,032 certain saccharide esters of menthol are proposed as additives to tobacco. In French Pat. No. 1,572,332 N,N-dimethyl 2-ethylbutanamide is reported as having a minty odour and refreshing effect, and the minty odour of N,N-diethyl 2,2-dimethylpropanamide is also referred to. A similar effect is reported for N,N-diethyl 2-ethylbutanamide in Berichte 39, 1223, (1906). A minty odour has also been reported for 2,4,6-trimethylheptan-4-ol and 2,4,6-trimethyl hept-2-en-4-ol in Parfums-Cosmetiques-Savons, May 1956, pp. 17–20. The cooling effect of menthol and other related terpene alcohols and their derivatives has also been studied and reported in Koryo, 95, (1970), pp. 39–43. 2,4-p-menthane diol has also been reported as having a sharp cooling taste (Beilstein, Handbuch der Organischen Chemie, fourth Ed. (1923) Vol. 6, p. 744.). Still other substituted p-menthanes having a physiological cooling effect are disclosed in German Offenlegungsschrift Nos. P 22 02 535, P 22 03 947, P 22 03 273 and P 22 05 255.

Despite this knowledge of other compounds having an odour and flavour similar to that of menthol, menthol is still extensively used in topical, ingestible and other compositions notwithstanding the disadvantages mentioned above, namely its very strong odour and its relative volatility.

OBJECTS OF THE INVENTION

It is an object of the present invention to provide other compounds having a pronounced physiological cooling effect, in many cases far more persistent than that obtained with menthol, without the attendant disadvantages of a strong minty odour but with alternative odours.

It is a further object to provide compounds having a pronounced physiological cooling effect and being of relatively low volatility.

It is a further object of the present invention to provide ingestible, topical and other compositions capable of stimulating the cold receptors of the nervous system of the human body thereby to create a desirable 'cool' sensation, and a method of making them.

It is a yet further object of the present invention to provide a method of stimulating the cold receptors of the nervous system of the body to create a cool sensation.

Other objects will be apparent from the following detailed description of the invention.

SUMMARY OF INVENTION

The present invention is based on the discovery of a group of primary alcohols which have a pronounced physiological cooling activity, but which are without the strong minty odour characteristic of menthol having instead rather different odours mainly of a camphoraceous nature and which are of relatively low volatility and which are substantially non-toxic. These compounds are primary alcohols of the formula:

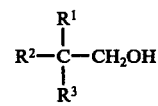

where
$R^1$ is $C_2$–$C_6$ alkyl;
$R^2$ is $C_2$–$C_5$ alkyl; or $C_2$–$C_5$ alkenyl;
$R^3$ is H or $C_1$–$C_5$ alkyl;
with the provisos that
i. the total number of carbon atoms in the molecule is from 8–14, preferably 8–12, inclusive;
ii. $R^1$ and $R^2$ may also be joined to form, together with the carbon atom to which they are attached, a saturated monocyclic hydrocarbon group containing up to 11 ring carbon atoms;
iii. when $R^1$ and $R^2$ are so joined and with the carbon atom to which they are attached form a p-menthyl group, then $R^3$ is $C_1$–$C_5$ alkyl;
iv. when $R^1$ and $R^2$ are so joined and $R^3$ is H then the carbocyclic ring shall contain at least one alkyl substituent; and
v. when $R^1$ and $R^2$ are separate groups and $R^3$ is H then at least one of $R^1$ and $R^2$ shall have branching in an alpha or beta position.

STATEMENT OF INVENTION

In accordance with this invention, therefore, there are provided consumer products for application to or consumption by the human body comprising a consumer product base and a means for stimulating the cold receptors of the nervous system of the human body wherein said means comprise an effective amount of one or more primary alcohols of the formula hereinbefore set forth.

By consumer product we mean a manufacturered product applied to or consumed by the human person for toilet, cosmetic, hygienic, nutritive, curative, prophylactic, or other purposes and constituting a vehicle by means of which the said primary alochols may be brought into contact with the skin, mucous membranes or other surface tissues of the body, whether external tissues or internal, for example, of the nose, throat, mouth and gastrointestinal tract, and includes liquid and solid phase preparations of an essentially formless nature e.g. solutions, emulsions, pastes, ointments, powders etc., solid phase preparations of semi-permanent form, e.g. shaped toilet and cosmetic preparations and shaped edible preparations, whose shaped form is only temporary and which lose that form on use, and articles of permanent form but which are of an essentially disposable nature, e.g. cleansing tissues, toothpicks etc.

Typical consumer products into which the primary alcohols may be incorporated in accordance with this invention and which may therefore serve as vehicles for application of the compounds to the person are:

1. Edible and potable compositions including alcoholic and non-alcoholic beverages; confectionary; chewing gum; cachous; ice cream; jellies;

2. Toiletries including after-shave lotions, shaving soaps, creams and foams, toilet water, deodorants and antiperspirants, 'solid colognes', toilet soaps, bath oils and salts, shampoos, hair oils, talcum powders, face creams, hand creams, sunburn lotions, cleansing tissues, dentifrices, toothpicks, mouthwashes, hair tonics, eyedrops;

3. Medicaments including antiseptic ointments, pile ointments, liniments, lotions, decongestants, counter-irritants, cough mixtures, throat lozenges, antacid and indigestion preparations, oral analgesics;

4. Miscellaneous compositions such as water soluble adhesive compositions for envelopes, postage stamps, adhesive labels etc.

DETAILED DESCRIPTION

Many of the primary alcohols used in accordance with this invention are known compounds and some are commercially available. They may, in general be prepared by procedures well known in the art for the preparation of alcohols, for example, by the reduction, using lithium aluminium hydride of carboxylic acids, acid chlorides or esters of the type:

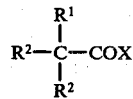

where $R^1$, $R^2$ and $R^3$ are as above defined and X is —OH, —Cl or —OR, where R is lower, e.g. $C_1$–$C_5$, alkyl.

Many of the compounds used as cold receptor stimulants in accordance with this invention exhibit either geometric or optical isomerism or both and, depending on the starting materials and the methods used in their preparation the compounds may be isomerically pure, i.e. consisting of one geometric or optical isomer, or they may be isomeric mixtures, both in the geometric and optical sense. Generally, the compounds will be used as isomeric mixtures, but in some cases the cooling effect may differ as between geometric or optical isomers, and therefore one or other isomer may be preferred.

The cooling sensation created by the compounds used in this invention on the skin and mucous membranes, for example, in the mouth, varies both in intensity and longevity from compound to compound. Amongst the most preferred compounds used in accordance with this invention are cyclic compounds containing 5, 6 or 7 ring carbon atoms, a total of from 10–12 carbon atoms and having an alpha-branched $C_3$–$C_5$ alkyl group in a 1 or 2-position in the ring. Typical cyclic compounds in this preferred group are:

(1-isopropyl-2-methylcyclopentyl) methanol
(1-isopropylcycloheptyl) methanol
(1-sec.butylcycloheptyl) methanol
(2-isopropylcycloheptyl) methanol
(1-isopropyl-2-methylcycloheptyl) methanol
(1-isopropylcyclohexyl) methanol.

Preferred acyclic compounds are those containing a total of from 8–12 carbon atoms, $R^3$ is H or $C_1$–$C_5$ straight chain alkyl and at least one of $R^1$ and $R^2$ has branching in an alpha position. Typical acyclic compounds in this preferred group are 2,2,4-trimethylpent-3-yl methanol
2-methyl-3-ethylpent-3-yl methanol
2,4-dimethylpent-3-yl methanol
2,4-dimethyl-3-ethylpent-3-yl methanol.

For the purposes of the present disclosure the following test procedure has been devised as a means to identify compounds having a physiological cooling activity in accordance with the present invention and herein referred to as cold receptor stimulants. This test is intended purely as a means for identifying compounds having a physiological cooling activity and useful in the present invention and for giving an indication of the different relative activities of the compounds, as between themselves and as compared with menthol, when applied in a particular manner to a particular part of the body. The results are not necessarily indicative of the activity of these compounds in other formulations and other parts of the body where other factors come into play. For example, a controlling factor in the onset of cooling effect, its intensity and longevity will be the rate of penetration of the compounds through the epidermis and this will vary in different locations on the human body. The formulation of actual products according to this invention will therefore be done largely on an empirical basis although the test results and other figures given herein will be useful as a guide, particularly in the formulation of products for oral administration, since the test procedure to be described involves oral application of the compound. A similar test may, of course, be devised for the purposes of measuring the relative activities of the compounds on another area of the body, for example, the face or forearm, and this will be a useful guide in the choice of compounds to be used in preparation for external topical usage.

It will also be noted that the described test procedure is done on a statistical basis. This is necessary since sensitivity to these compounds will vary not only from compound to compound and from one part of the body to another, but also from one individual to another.

Tests of this nature are commonly used in the testing of the organoleptic properties, e.g. taste, smell etc. of organic and inorganic compounds, see Kirk-Othmer: Encyclopedia of Chemical Technology, second Ed. (1967) Vol. 14 pages 336–344.

TEST PROCEDURE

The following test procedure is aimed at determining the minimum quantity of the test compound required to produce a noticeable cooling effect on a person of average sensitivity, this minimum quantity being termed the threshold for that particular compound. The tests are carried out on a selected panel of 6 people of median sensitivity to 1-menthol.

PANEL SELECTION

To select a test panel of average sensitivity the following procedure is used. Known quantities of 1-menthol in solution in petroleum ether (bp. 40–60) are placed on 5 mm squares of filter paper, whereafter the solvent is allowed to evaporate. A panel of observers is enrolled and asked to place one impregnated square at a time on the tongue and to report on the presence or absence of a cooling effect. The quantity of 1-menthol on each impregnated square is gradually reduced from a value substantially above 0.25 µg per square to substantially below 0.25 µg, the precise range being immaterial. Conveniently, one starts with squares containing 2.0 µg 1-menthol, the amount on each successive square being half that of the preceding square, i.e. the second test square will contain 1.0 µg, the third 0.5 µg and so on. Each quantity is tested on the tongue at least 10 times. In this way, the thresholds to cold receptor stimulus by 1-menthol are determined for each individual of the panel, the threshold for each individual being that amount of 1-menthol for which, in a series of not less than 10 test applications, a cooling effect is reported 50% of the time. Six panel members are now selected whose threshold to 1-menthol is in the range 0.1 µg to 10 µg and whose average threshold is approximately 0.25 µg, this select panel being regarded as the test panel of average sensitivity.

COMPOUND TESTING

To test the activity of compounds according to this invention, the above procedure is repeated using only the 6 selected panel members of average sensitivity to 1-menthol. The individual thresholds for each test compound on each of the 6 selected panel members are determined and averaged. Those compounds whose average threshold on the select test panel is 100 µg or less are regarded as having cooling activity in accordance with this invention.

TEST RESULTS

The following table sets out the relative cooling activities of compounds of the formula defined above when tested according to the foregoing procedure.

Table

| Compound | Threshold (Mg) |
| --- | --- |
| (2-isopropylcycloheptyl) methanol | 1 |
| 2,2,4-trimethylpent-3-yl methanol | 1 |
| (1-isopropyl-2-methylcyclopentyl) methanol | 2 |
| (1-sec.butylcycloheptyl) methanol | 2 |
| (1-isopropyl-2-methylcycloheptyl) methanol | 2 |
| (1-isopropylcycloheptyl) methanol | 4 |
| (1-isopropylcyclohexyl) methanol | 4 |
| (2,2,6-trimethylcyclohexyl) methanol | 5 |
| n-hept-3-yl methanol | 5 |

Table-continued

| Compound | Threshold (Mg) |
| --- | --- |
| 2,2-dimethyl-hex-5-en-3-yl methanol | 6 |
| 2,6,6-trimethylcycloheptyl) methanol | 6 |
| (1,2-diethylcyclohexyl) methanol | 7 |
| 2-methyl-3-ethylpent-3-yl methanol | 7 |
| 2,4-dimethylpent-3-yl methanol | 8 |
| 2,4-dimethyl-3-ethylpent-3-yl methanol | 8 |
| (1-ethyl-2-methylcyclohexyl) methanol | 9 |
| (1-ethylcycloheptyl) methanol | 10 |
| (3-ethyl-p-menth-3-yl) methanol | 15 |
| (3,3,5,5-tetramethylcyclohexyl) methanol | 18 |
| 2,4,6-trimethylhept-4-yl methanol | 20 |
| (1-ethylcycloundecyl) methanol | 20 |
| (4-tert.butylcyclohexyl) methanol | 20 |
| (1-n-butyl-2,3-dimethylcyclohexyl) methanol | 50 |
| 3,4,5-trimethylhept-4-yl methanol | 50 |

The cold receptor stimulants used in this invention find utility in a wide variety of consumer products for consumption by or application to the human body. Broadly speaking, these products can be divided into ingestibles and topicals, both terms being taken in their broadest possible sense. Thus ingestible is to be taken as including not only foodstuffs and beverages taken into the mouth and swallowed, but also other orally ingested products taken for reasons other than their nutritional value, e.g. indigestion tablets, antacid preparations, laxatives, etc. Ingestible is also to be taken to include edible compositions taken by mouth, but not necessarily swallowed, e.g. chewing gum. Topical is to be taken as including not only compositions such as perfumes, powders and other toiletries, lotions, linaments, oils and ointments, applied to the external surfaces of the human body, whether for medical or other reasons, but also compositions applied to, or which, in normal usage, come in contact with, internal mucous membranes of the body, such as those of the nose, mouth or throat, whether by direct or indirect application, mouthwash and gargle compositions. Topical products, in this context, also include toilet articles such as cleansing tissues and toothpicks.

In formulating the products of this invention the cold receptor stimulants will be incorporated into a vehicle by means of which the compound may be applied to the person. The vehicle may, itself be completely inert or it may, and usually will, contain other active ingredients. A wide variety of vehicles will be suitable, depending upon the particular product involved, such vehicles including solids, liquids, emulsions, foams and gels. Typical vehicles for the cold receptor stimulants include aqueous or alcoholic solutions, oils and fats such as hydrocarbon oils, fatty acid esters, long chain alcohols and silicone oils; finely divided solids such as starch or talc; cellulosic materials such as paper tissue; low-boiling hydrocarbons and halohydrocarbons used as aerosol propellants; gums and natural or synthetic resins.

Generally, these vehicles will contain at least one or more of the following adjuvants: flavourants, colourants, perfuming agents, surface active agents, antiseptic agents, such as are usually employed in topical and ingestible compositions.

A more detailed discussion of particular products according to this invention follows.

TOILETRIES AND COSMETICS

A major area of utility of the cold receptor stimulants of this invention will be in the field of toilet preparations broadly classed as personal care products. These may be defined as manufactured products applied to the person for the purposes of grooming or hygiene or for cosmetic purposes, including make up and perfumery, but excluding ethical and proprietary medical preparations. Particular personal care products are discussed hereinafter by way of example and are illustrated hereinafter in the specific examples.

One class of personal care product into which the compounds of this invention may be incorporated is represented by lotions for topical application, e.g. aftershave lotions, toilet water etc. where the compound will be used in alcoholic or aqueous alcoholic solution, such solutions usually also containing a perfume or mild antiseptic or both. The amount of compound added to the formulation will usually be in the range 0.1 to 10% by weight based on the total composition.

Another class of personal care product is represented by soap and soap-based compositions where the compounds will be used in combination with an oil or fat or a natural or synthetic surfactant e.g. a fatty acid salt or a laurylsulphate salt, the composition usually also containing an essential oil or perfume. The range of soap compositions will include soaps of all kinds e.g. toilet soaps, shaving soaps, shaving foams etc. particularly shaving foams of the aerosol type. Usually the compound will be added to the formulation in amount of from 1 to 10% by weight.

A further class of personal care products into which the cold receptor stimulants may be incorporated is represented by cosmetic creams, emollients and lotions, such creams, emollients and lotions usually comprising an oil-in-water emulsion as a base and optionally containing a range of other ingredients such as wax, preservative, perfume, antiseptics, astringents, pigments etc. Also included within this class are lipstic compositions, such compositions usually comprising an oil and wax base into which the coolant can be incorporated along with other ingredients e.g. pigments. Once again the formulation of such products, apart from the incorporation of the cold receptor stimulant, usually in an amount of from 0.05 to 10% by weight, is conventional.

Personal care products for oral hygiene into which the cold receptor stimulants of this invention can be incorporated include mouthwash, gargle and dentifrice compositions. The first two may be considered together and will usually comprise an aqueous, alcoholic or aqueous-alcoholic solution of an antiseptic often coloured or flavoured for palatability, to which the cold receptor stimulant is added in an amount of from 0.01 to 10% by weight.

Dentifrice compositions may be of the solid block, powder, paste or liquid type and will usually comprise a finely divided abrasive or polishing material, e.g. precipitated chalk, silica, magnesium silicate, aluminium hydroxide or other similar materials well known in the art, and a detergent or foaming agent. Optional ingredients which may also be included are flavouring agents and colourants, antiseptics, lubricants, thickeners, emulsifiers or plasticizers. The amount of cold receptor stimulant added in such compositions will generally be from 0.1 to 5.0% by weight based on the total composition.

EDIBLE AND POTABLE COMPOSITIONS

The cold receptor stimulants of this invention may be incorporated into a wide range of edible and potable compositions comprising an edible or potable base and usually one or more flavouring or colouring agents. The particular effect of the cold receptor stimulant is to create a cool or fresh sensation in the mouth, and in some cases, even in the stomach, and therefore the compounds find particular utility in sugar-based confectionary such as chocolate, boiled sweets, mints and candy, in ice cream and jellies and in chewing gum. The formulation of such confections will be by traditional techniques and according to conventional recipes and as such forms no part of this invention. The cold receptor stimulant will be added to the recipe at a convenient point and in amount sufficient to produce the desired cooling effect in the final product. As already indicated, the amount will vary depending upon the particular compound, the degree of cooling effect desired and the strength of other flavourants in the recipe. For general guidance, however, amounts in the range 0.1 to 5.0% by weight based on the total composition will be found suitable.

Similar considerations apply to the formulation of beverages. Generally speaking the compounds will find most utility in soft drinks, e.g. fruit squashes, lemonade, cola etc., but may also be used in alcoholic beverages. The amount of compound used will generally be in the range 0.05 to 2.5% by weight based on the total composition.

MEDICAMENTS

Because of their cooling effect on the skin and on the mucous membranes of the mouth, throat and nose and of the gastrointestinal tract the cold receptor stimulants may be used in a variety of oral medicines, nasal and throat sprays, and topical compositions, particularly where a counter-irritant is required. Generally speaking, these medical preparations, whether topical or ingestible proprietary or ethical, will contain a pharmaceutically acceptable carrier, either liquid or solid, a pharmaceutically active ingredient and into these preparations the cold receptor stimulants of this invention can readily be incorporated to provide a pleasant cooling effect on the skin, or other surface tissues of the body, or in the mouth or gastrointestinal tract depending on particular preparation and whether it is to be applied externally or internally. A particular utility for the compounds of this invention is in the formulation of antacid and indigestion remedies, and especially those based on sodium bicarbonate, magnesium oxide, calcium or magnesium carbonate, aluminium or magnesium hydroxide or magnesium trisilicate. In such compositions the compound will usually be added in an amount of from 0.1 to 2.0% by weight.

The cold receptor stimulants may also be included in oral analgesic compositions e.g. with acetyl salicylic acid or its salts, and in nasal decongestants e.g. those containing ephedrine.

Consumer products according to the invention are illustrated by the following Examples in which all percentages are by weight.

EXAMPLE 1

After Shave Lotion

An after shave lotion was prepared according to the following recipe by dissolution of the ingredients in the liquid and cooling and filtering:

| | |
|---|---|
| Denatured ethanol | 75% |
| Diethylphthalate | 1.0% |
| Propylene Glycol | 1.0% |
| Lactic Acid | 1.0% |
| Perfume | 3.0% |

-continued

| | |
|---|---|
| Water | to 100% |

Into the base lotion was added 3% by weight based on the total composition of 2,4-dimethylpent-3-yl methanol.

When the final lotion is applied to the face a clearly noticeable cooling effect becomes apparent after a short interval of time.

EXAMPLE 2

Eye Lotion An eye lotion was prepared containing the following ingredients:

| | |
|---|---|
| Witch Hazel | 12.95% |
| Boric Acid | 2.00% |
| Sodium Borate | 0.50% |
| Allantoin | 0.05% |
| Salicylic Acid | 0.25% |
| Chlorobutol | 0.02% |
| Zinc Sulphate | 0.004% |
| Water | to 100% |

To the formulation was added 0.01% based on the total composition, of 2-methyl-3-ethylpent-3-yl methanol. When used to bathe the eyes a cool fresh sensation is apparent on the eyeball and eyelids.

EXAMPLE 3

Toothpaste

The following ingredients were mixed in a blender;

| | |
|---|---|
| Dicalcium Phosphate | 48.0% |
| Sodium Lauryl Sulphate | 2.5% |
| Glycerol | 24.8% |
| Sodium Carboxymethyl Cellulose | 2.0% |
| Citrus Flavourant | 1.0% |
| Sodium Saccharin | 0.5% |
| Water | to 100% |

Shortly before completion of the blending operation 1% by weight of 2,4-dimethyl-3-ethylpent-3-yl methanol was added to the blender.

When applied as a toothpaste, a cooling effect is noticed in the mouth.

EXAMPLE 4

Aerosol Shaving Soap

An aerosol shaving soap composition was formulated according to the following recipe:

| | |
|---|---|
| Stearic acid | 6.3% |
| Lauric acid | 2.7% |
| Triethanolamine | 4.6% |
| Sodium carboxymethyl cellulose | 0.1% |
| Sorbitol | 5.0% |
| Perfume | 0.4% |
| Water | to 100% |

The composition was prepared by fusing the acids in water, adding the triethanolamine, cooling and adding the other constituents. To the mixture was then added 2%, based on the total composition of (1-isopropylcyclohexyl) methanol. The composition was then packaged in an aerosol dispenser under pressure of a butane propellant.

When used in shaving a fresh cool sensation was distinctly noticeable on the face.

EXAMPLE 5

Toilet Water

A toilet water was prepared according to the following recipe:

| | |
|---|---|
| Denatured ethanol | 75.0% |
| Perfume | 5.0% |
| Water | to 100% |

To the recipe was added 4.0% based on the total composition, of 2,4-dimethyl-3-ethylpent-3-yl methanol.

As with the after shave lotion, a cooling effect was clearly noticeable on the skin well after the termination of any cooling effect attributable to the evaporation of the alcoholic carrier.

EXAMPLE 6

Soft Sweet

Water was added to icing sugar at 40° C to form a stiff paste. 1.0% of 2,4-dimethylpent-3-yl methanol was then stirred into the paste and the mixture allowed to set. A soft sweet mass resulted having the characteristic cooling effect in the mouth of peppermint but without the minty flavour or odour.

EXAMPLE 7

Indigestion Tablet

The following ingredients were ground together:

| | |
|---|---|
| Magnesium carbonate | 49.5% |
| Sorbitol | 49.4% |
| Saccharin | 0.1% |
| Talc | 1.0% |

Added to the mixture during grinding was 0.10% of (1-isopropylcyclohexyl) methanol. After mixing the mixture was pressed into 0.5 g tablets. Taken by mouth and swallowed the tablets produced, after a short interval of time, a noticeable cooling effect in the stomach.

EXAMPLE 8

Cleansing Tissue

A cleansing liquid was prepared having the formulation:

| | |
|---|---|
| Triethanolamine lauryl sulphate | 1.0% |
| Glycerol | 2.0% |
| Perfume | 0.95% |
| Water | to 100% |

To this liquid was added 4% of 2,4,6-trimethyl-hept-4-yl methanol. A paper tissue was then soaked in the liquid.

When the impregnated tissue was used to wipe the skin a fresh cool sensation developed on the skin after a short interval.

EXAMPLE 9

Hydrophilic Ointment

A hydrophilic ointment was prepared having the following formulation:

| | |
|---|---|
| Propylene Glycol | 12% |

| | |
|---|---|
| 1-Octadecanol | 25% |
| White Soft Paraffin | 25% |
| Sodium lauryl sulphate | 1% |
| Water | to 100% |

The sodium lauryl sulphate was added to the water and heated to 60° C. The paraffin was melted by heating to 60° C and was then added to the sodium lauryl sulphate mixture with stirring. Propylene glycol and 1-octadecanol were then added to this mixture.

To the resultant mixture was added 3% of (1-isopropylcyclohexyl) methanol. The final ointment when applied to the skin gave rise to a marked cooling effect.

EXAMPLE 10

Vapour Rub

4% of (1-isopropyl-2-methylcyclopentyl) methanol was mixed into 96%, of soft white paraffin. When rubbed onto the skin a pleasant cooling vapour is released.

EXAMPLE 11

Deodorant Composition

A deodorant composition suitable for formulation and dispensing as an aerosol under pressure of a suitable propellant was formulated according to the following recipe:

| | |
|---|---|
| Denatured ethanol | 96.9% |
| Hexachlorophene | 2.0% |
| Isopropyl myristate | 1.0% |
| Perfume | 0.1% |

To the composition was added 4% by weight of (2-isopropylcycloheptyl) methanol. Application of the final composition gave rise to a definite cooling sensation on the skin.

EXAMPLE 12

Hair Shampoo

Sodium lauryl ether sulphate, 10 g, was dispersed in 90 g water in a high speed mill. To the dispersion was added 4.5% by weight of (1-sec.butylcycloheptyl) methanol. When the hair is washed using the shampoo, a fresh, cool sensation is noticed on the scalp.

EXAMPLE 13

Lipstick 0.1% by weight of 2,2,4-trimethylpent-3-yl methanol was incorporated into a proprietary lipstick by melting the lipstick, adding the compound, and allowing the lipstick to resolidify. When applied to the lips a persistant cooling effect is clearly noticeable.

EXAMPLE 14

Solid Cologne

A solid cologne was formulated according to the following recipe:

| | |
|---|---|
| Denatured ethanol | 74.5% |
| Propylene glycol | 3.0% |
| Sodium stearate | 5.0% |
| Perfume | 5.0% |
| Water | to 100% |

The sodium stearate was dissolved by stirring in a warm mixture of the ethanol, propylene glycol and water. To the solution was added the perfume and 4% of (1-isopropylcyclohexyl) methanol and the mixture then allowed to solidify into a waxy cake.

When applied to the forehead a strong cooling effect is obtained.

EXAMPLE 15

Hair Tonic

A hair tonic was formulated containing:

| | |
|---|---|
| Denatured ethanol | 84.5% |
| Caster Oil | 14.0% |
| Resorcinol | 0.5% |
| Perfume | 1.0% |

The caster oil, resorcinol and perfumes were dissolved in the ethanol component and to the solution was added 4% of 1-ethyl-2-methylcyclohexyl) methanol. When rubbed on the scalp a cooling effect is noticed.

EXAMPLE 16

Mouthwash

A concentrated mouthwash composition was prepared according to the following recipe:

| | |
|---|---|
| Ethanol | 3.0% |
| Borax | 2.0% |
| Sodium bicarbonate | 1.0% |
| Glycerol | 10.0% |
| Flavourant | 0.4% |
| Thymol | 0.03% |
| Water | to 100% |

To the composition was added 0.5% of (2,2,6-trimethylcyclohexyl) methanol.

When diluted with approximately 10 times its own volume of water and used to rinse the mouth a strong cooling effect is obtained in the mouth.

EXAMPLE 17

Toothpicks

The tip of a wooden toothpick was impregnated with an alcoholic solution containing (1-sec.butylcycloheptyl) methanol in sufficient amount to deposit on the toothpick, 0.1 mg of the alcohol. The impregnated toothpick was then dried. When placed on the tongue there is no detectable taste, however, a distinct cooling effect is noticeable after a short period of time.

EXAMPLE 18

Talcum Powder

A talcum powder was prepared by grinding together the following:

| | |
|---|---|
| Low micron talc | 90% |
| Zinc stearate | 5% |
| Starch | 5% |

In the course of grinding there was added 5% of (2-methyl-1-isopropylcycloheptyl) methanol. A talcum powder having a freshening and cooling effect was obtained.

EXAMPLE 19

Soft Drink

A soft drink concentrate was prepared from the following recipe:

| | |
|---|---|
| Pure orange juice | 60% |
| Sucrose | 10% |
| Saccharin | 0.2% |
| Orange flavouring | 0.1% |
| Citric acid | 0.2% |
| Sulphur dioxide | trace amount |
| Water | to 100% |

To the concentrate was added 0.1% of (2-isopropylcycloheptyl) methanol.

The concentrate was diluted with water and tasted. An orange flavour having a pleasantly cool after-effect was obtained.

EXAMPLE 20

Chewing Gum

Leaves of a proprietary chewing gum were leached in running water for 168 hours to remove all water-soluble flavourants. At the end of the leaching operation the chewing gum base had no detectable minty odour or flavour. The chewing gum base was then kneaded with 0.2% of (2-methyl-1-isopropylcycloheptyl) methanol. When compared with the water-extracted chewing gum base, the final product showed no distinguishable change in flavour but showed a marked cooling effect in the mouth.

The above Examples illustrate the range of compounds and the range of compositions included within the present invention. However, they are not to be taken as limiting the scope of the invention in any way. Numerous other compounds within the general formula will be equally suitable for use in the compositions of Examples 1–20 and the physiological cooling effect obtained with the compounds of the invention will recommend their use in a wide variety of other compositions where the cooling effect will be of value.

The substituted methanols hereinbefore referred to as cold receptor stimulants in ingestible and topical compositions also find utility as cold receptor stimulants in tobacco and tobacco-containing manufactures.

As has already been mentioned, menthol is extensively used for this purpose notwithstanding its strong minty odour and relative volatility. Other similar compounds have also been proposed as alternatives to menthol in tobacco, see for example, the various publications hereinbefore referred to. Still other compounds have been proposed as 'flavourants' in tobacco rather than 'coolants' and amongst these may be mentioned 2-isopropyl-5-methyl hexanol (alternatively named 2,6-dimethylhept-3-yl methanol) and related compounds as disclosed in U.S. Pat. No. 3,704,714. Notwithstanding these various disclosures a need still exists for alternatives to menthol for incorporating into tobacco to provide a 'cool' effect when smoked.

It is a further object of the present invention, therefore, to provide tobacco and tobacco-containing manufactures containing an ingredient which creates a 'cool' sensation when the ingredient comes into contact with the nasal and oral mucosa, either in the tobacco smoke, or by direct contact of the tobacco on the nasal or oral mucosa, but which are not subject to the disadvantages of a strong minty flavour and storage instability.

It is a yet further object of the present invention to provide an improved method of imparting to tobacco and tobacco-containing manufactures a physiological cooling activity.

According to the present invention, therefore, there are also provided tobacco and tobacco-containing manufactures comprising tobacco and a cold receptor stimulating additive, present in an amount effective to stimulate the cold receptors of the nervous system of mucous membranes of the oral and nasal mucosa when the tobacco or tobacco-containing manufacture is smoke, chewed or inhaled by the human user, said additive being a cold receptor stimulating substituted methanol of the formula hereinbefore defined, subject to the following further proviso, namely that when one of $R^1$ and $R^2$ is isoamyl and the other is isopropyl, then $R^3$ shall be $C_1$–$C_5$ alkyl.

By tobacco and tobacco-containing manufactures we means any article, such as a cigarette or cigar, or any composition, such as pipe or chewing tobacco or snuff, containing tobacco in a prepared form ready for utilisation by the human person whether by smoking, i.e. burning of the prepared tobacco and inhalation of the tobacco smoke, chewing or direct inhalation of the tobacco.

In formulating the tobacco and tobacco-containing manufactures of this invention the active compound may be incorporated directly into the tobacco, for example, by impregnation of the tobacco with an alcoholic solution of the active ingredient, at a suitable stage of manufacture. However, in an alternative and preferred arrangement, the active ingredient may be incorporated into a tobacco smoke filter for use in a pipe or cigarette filter or as a filter tip for cigarettes. The latter, in particular, forms a particularly effective utilisation of the present invention, the active compound simply being impregnated in the wad of material forming the filter tip. This may be any of the well known types of filter tip for cigarettes, e.g. a filter pad of cellulose acetate, paper, cotton, α-cellulose or asbestos fiber. Conveniently the filter tip is impregnated with an alcoholic solution of the active compound and then dried to deposit the active compound therein.

The amount of active compound to be incorporated into the tobacco or tobacco-containing manufacture in accordance with the invention will vary from compound to compound depending on the activity thereof, i.e. the amount thereof which it is necessary to place in contact with the skin to produce a noticeable cooling effect, and will depend also on the mode of application thereof, i.e. whether the compound is impregnated in the tobacco itself, or in a filter tip or in any other accessory. However, the actual amount is not critical to this invention and will be readily determinable by the person skilled in the art by means of a few simple tests. As a matter of guidance, however, it may be mentioned that with the more active compounds, as little as 0.01 mg deposited on the filter tip of a tipped cigarette is effective.

This latter aspect of the invention is illustrated by the following Examples.

EXAMPLE 21

Cigarette Tobacco

A proprietary brand of cigarette tobacco was sprayed with an ethanolic solution of 2-methyl-3-ethylpent-3-yl methanol and was rolled into cigarettes each containing approximately 2.0 micrograms of active compound. Smoking the impregnated cigarettes produced a cool effect in the mouth characteristic of mentholated cigarettes but without any attendant odour other than that normally associated with tobacco.

EXAMPLE 22

Filter Tip Cigarettes

The filter tip of a proprietary brand of cigarette was impregnated with an ethanolic solution of (1-isopropylcyclohexyl) methanol in an amount sufficient to deposit in the filter 0.02 mg of the active compound. Smoking the cigarette with the impregnated tip gave rise to a noticeable cooling effect in the mouth.

EXAMPLE 23

Pipe Tobacco

A proprietary brand of pipe tobacco was sprayed with an ethanolic solution of (1-isopropyl-2-methylcycloheptyl) methanol 2g of the tobacco containing 12 mg of the active compound was placed in a pipe. Smoking the impregnated tobacco produced a cool effect in the mouth characteristic of mentholated tobacco but without any attendant odour other than that normally associated with tobacco.

EXAMPLE 24

Cigars

The tobacco of a proprietary brand of cigar was impregnated with an ethanolic solution of 2,2,4-trimethylpent-3-yl methanol in an amount sufficient to deposit in the cigar 2 mg of the active compound. Smoking the cigar with the impregnated tobacco gave rise to a noticeable cooling effect in the mouth.

EXAMPLE 25

Chewing Tobacco

A proprietary brand of chewing tobacco was impregnated with an ethanolic solution of (1-isopropyl-2-methylcyclopentyl) methanol; 1g of the tobacco containing 1.0 mg of active compound was used. Chewing the impregnated tobacco produced a cool effect in the mouth.

EXAMPLE 26

Snuff

A proprietary brand of snuff was impregnated with an ethanolic solution of (2-isopropylcycloheptyl) methanol. 1g of the snuff was impregnated with 8 mg of active compound. About 0.01 g of the impregnated snuff produced a cool effect in the nose when inhaled.

We claim:

1. In a manufactured consumer product for application to or consumption by the human body, said product comprising a topically administrable or orally ingestible vehicle and, as adjuvants in said vehicle, (i) at least one of the following: a flavourant, colourant, perfume, surface active agent or antiseptic, and (ii) a compound capable of stimulating the cold receptors of the nervous system in the surface tissues of the body, or in the mouth, when brought into contact therewith, respectively by topical application or oral ingestion of the said product, the improvement which comprises using as said cold receptor stimulating compound an effective amount of an alcohol of the formula

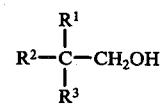

where
$R^1$ is $C_2-C_6$ alkyl;
$R^2$ is $C_2-C_5$ alkyl or $C_2-C_5$ alkenyl;
$R^3$ is H or $C_1-C_5$ alkyl;
with the provisos that the total number of carbon atoms in the molecule is from 8–12 and that at least on of $R^1$ and $R^2$ has branching in an alpha position.

2. A product according to claim 1 which is a personal care product containing an effective amount of said cold receptor stimulating compound.

3. A product according to claim 1 which is a chewing gum containing an effective amount of said cold receptor stimulating compound.

4. A method of stimulating the cold receptors of the nervous system of the human body which comprises applying thereto an effective amount of an alcohol of the formula defined in claim 1.

* * * * *